United States Patent [19]

Vernes et al.

[11] Patent Number: 5,286,483
[45] Date of Patent: Feb. 15, 1994

[54] 50 KILODALTON ANTIGEN OBTAINED FROM THE INTRAERYTHROCYTIC PHASE OF PLASMODIUM FALCIPARUM

[76] Inventors: Alain Vernes, 20 Facade de l'Esplanade, 59 800 Little; François J. Dubrometz, 6 rue de la Coquerie, 59 310 Nomain; Bernard Fortier, A 1, Place du Maréchal Leclerc, 59 800 Little; Patrick Deplace, 25 Square du Portugal, 59 000 Little, all of France

[21] Appl. No.: 660,263

[22] Filed: Feb. 26, 1991

Related U.S. Application Data

[63] Continuation-in-part of Ser. No. 924,078, Oct. 27, 1986, abandoned.

[30] Foreign Application Priority Data

Oct. 28, 1985 [FR] France ................ 85 15986

[51] Int. Cl.$^5$ .......................................... A61K 39/002
[52] U.S. Cl. ..................................... 424/88; 435/947; 530/350; 530/822
[58] Field of Search .............. 530/350, 395, 820, 822; 424/88; 435/68.1, 947

[56] References Cited

U.S. PATENT DOCUMENTS

| | | | |
|---|---|---|---|
| 4,767,622 | 8/1988 | Ristic et al. | 424/88 |
| 4,835,259 | 5/1989 | Reese et al. | 530/395 |
| 5,116,755 | 5/1992 | Kemp et al. | 435/252.3 |

OTHER PUBLICATIONS

A. Bhatra et al. Am. J. Trop. Med. Hyg. 36:15–19 1987.
Lyon & Haynes P.falerparum Ag Synthesized by Schezonts . . . J. Immunology 136(6):2245-2251 Mar. 15, 1986.
Weber et al., Molecular Strategies of Parasitic Invasion, 1987 Alan R. Liss Inc., pp. 379–388.
Ravetch et al, Bio/Technology vol. 3, 1985, pp. 729–740
Ramasamy et al, J. Immunol. 134(3) 1985, pp. 1952–1955.
Holder et al, Nature 317, 1985, pp. 270–273.
Holder et al Nature, 294, 1981 pp. 361–364.
Mc Garvey et al PNAS 81, 1984, pp. 3690–3694.
Wiser, Eur J. Cell Biol 42, 1986, pp. 45–51.
Hall et al Nature 311, 1984, pp. 379–382.
Lyon et al PNAS 83, 1986, pp. 2989–2993.
De Silva; Bull WHO 61, 1983, pp. 105–112.
Lyon et al, J Immunol 136(1) 1986, pp. 2253–2258.
Odink et al FEBS 1984 vol. 173(1) pp. 108–112.
Delplan et al CA vol. 103, 1985, #212 923y.
Person et al, J Immunol 134(3) 1985, pp. 1946–1951.
Myler et al., CA vol. 99, 1983, #15009C.

*Primary Examiner*—Garnette D. Draper
*Assistant Examiner*—Lorraine M. Spector
*Attorney, Agent, or Firm*—Larson and Taylor

[57] ABSTRACT

The invention concerns antigens from the intraerythrocytic phase of *Plasmodium falciparum*, namely: a protein of 50 kDa with an isoelectric point of 5.5 and a protein of 65 kDa separated by electrophoresis in reducing conditions into two polypeptides of 47 and 18 kDa, both appearing in the serum of patients infected by *Plasmodium falciparum* or in the culture medium of this microorganism during its intraerythrocytic phase, as well as a protein of 126 kDa synthesized during the nuclear multiplication phase during schizogony and localized on the periphery of the schizonts at the parasitophore vacuole level, precursor of the 50 kDa and 65 kDa proteins. Application of these proteins in the preparation of vaccines against malaria, and monoclonal antibodies corresponding to the assay of the antibodies of an immunized subject and assay of the antigens according to the invention during an attack of malaria.

3 Claims, No Drawings

50 KILODALTON ANTIGEN OBTAINED FROM THE INTRAERYTHROCYTIC PHASE OF PLASMODIUM FALCIPARUM

This application is a continuation-in-part of U.S. application Ser. No. 06/924,078 filed Oct. 27, 1986 now abandoned.

The invention concerns the surveillance of malaria, more particularly, the malaria caused by *plasmodium falciparum* which is the gravest form of this disease in man and vaccination against this disease.

More precisely, the invention concerns two proteins, the culture medium of *Plasmodium falciparum*, their precursor in the parasite, the assay of these proteins and their antibodies in the serum, as well as the vaccines using these proteins as active principle.

It will be recalled that malaria is a very widely distributed periodic fever in the world, often with fatal results, due to the protozoan of the *Plasmodium* type, in particular *Plasmodium falciparum*. The protozoan is transmitted to man by a mosquito (anopheles).

After a major regression due to the massive utilisation of insecticides on the one hand, and preventive and curative chemical treatments in man, on the other hand, the disease is progressing again due, on the one hand, to the resistance of insects to the most widely used insecticides and, on the other hand, to the progressive resistance of the disease itself to the widely used drugs such as quinine and nivaquine.

In view of these alarming findings, research aimed at controlling malaria is now directed towards developing a preventive treatment by vaccination, notably against the most dangerous form of this disease, that due to *plasmodium falciparum*.

It will be recalled that this parasite has a very complex life cycle. On biting, the mosquito injects into the bloodstream sporozoites which represent the infectious form of the parasite. The sporozoites then penetrate the liver where they multiply without any immune response. After some ten days they are released from the liver in the form of merozoites which infect certain red cells in which they multiply, which causes these red cells to burst with an onset of fever. The merozoites thus released attack other erythrocytes which results in further periodic onsets of fever.

Moreover, certain of the parasites derived from erythrocytes lead to a sexed form which infect the mosquito. These forms, after fertilization in the stomach of the insect, result in the formation of sporozoites, which migrate to the salivary glands of the insect thereby making it infectious.

In view of the life cycle of *Plasmodium falciparum*, the protection of exposed subjects could be envisaged either by means of an antisporozoite vaccine or an antimerozoite vaccine.

However, the first of these solutions appears to raise major problems in that vaccine has to be completely effective, that is, lead to the destruction of all these sporozoites that could penetrate the organism, failing which the infection could develop because of the production of merozoites and their multiplication in the absence of any specific antibodies.

The applicant therefore directed his research towards the development of an antimerozoite type vaccine which in particular could inhibit the reinvasion stage of the erythrocytes. He also interested himself in the development of tests making it possible, on the one hand, to study the immunization of subjects having on several occasions been in contact with the pathogen, and by an assay of their antibodies and, on the other hand, to follow the evolution of the disease, in particular during a chemical treatment.

With the aim of identifying and isolating antigens that could be used in the applications referred to above, the applicant interested himself more particularly in the products released from parasitized red cells.

More precisely, with the aim of identifying the *Plasmodium falciparum* exoantigens that could be immunologically active, the applicant purified the immunoglobulin derived from human plasma inhibiting in vitro the invasion of red cells by merozoites and used the purified extract for immunoprecipitating the products released in the culture medium by a synchronous culture of *Plasmodium falciparum* in the presence of $^{35}S$ labelled methionine at various stages of the schizogonic cycle.

In order to allow this cycle to be completed and the products synthesized by the parasite to be released completely, the applicant decided to study infected erythrocytes and the culture medium, both during labelling with $^{35}S$ methionine and during a prolonged period in non-labelled medium, called "cold medium", in which radioactive synthesis stopped. These two stages taken together are known as "pulse-chase".

This procedure is very different from the technique suggested by Rodriguez Da Silva et al. (ref. 18) see page 32 for carrying out a study of the same type and involving the analysis of cells and supernatants at the end of the labelling period of 6 hours.

The experimental details concerning this study are given in the experimental part (I) of this present memorandum.

The results obtained show that 4 major antigens (140, 126, 108 and 70 kDa) are recognized in the red cells by the immun IgG on completion of labelling. Two of these (126 and 108 kDa) disappeared during the first 12 hours of the "chase". In the culture media, a major product of 50 kDa (accompanied by a less intense compound of 47 kDa) appeared after 12 hours and then diminished. These two antigens are not found in the parasitized red cells.

Two-dimensional analysis by electrophoresis showed that the 50kDa band is formed by a single protein of pI 5.5, whereas the 47 kDa is separated into two spots of about 5.9 and 6.1.

Plasmodium antigens of protein nature whose molecular weights range in various intervals have already been mentioned in the literature.

Thus, European patent application EP-A-0.136.215 describes antigenic proteins which can be isolated from supernatant fluid medium washings including hypotonic washes. The molecular weights of these antigens rise in stages from 35,000 to 80,000 daltons and two immunogens considered as the principal ones respectively have a molecular weight of 42,000 and 54,000. An electrophoretic analysis reveals two bands of 56 kDa and 46 kDa in place of 49 kDa. It will be noted first of all that an indication merely of a molecular weight does not enable the antigens to be distinguished and it is usual to examine within a range of 1000 daltons around a given molecular weight, which represents the extreme limit of precision of the SDS PAGE analysis method, several distinct proteins of *Plasmodium* having no common antigenic specificity or functionality. If an attempt is made to define the antigens described in this previous publication, it is found that these latter are of a glycoprotein nature and that the antibodies synthesised by the experimentally immunized animals against these proteins, show that all the forms, including the young forms (rings) are labelled. In addition, human sera in vitro inhibit the invasion of healthy red cells by merozoites, which indicates that the target antigens are on the surface of the merozoites.

As the specification of the invention shows hereinafter, the antigens stated in the invention do not correspond to any of these characteristics.

The paper in EXPERIENTIA, vol. 40, N° 12, December 1984, pages 1343-1350, Basel CH; L. PERRIN et al.: "Malaria: immunity, vaccination and immunodiagnosis" enumerates antigens declared to be specific compared with the schizonts and/or merozoites, having different molecular weights rising in stages from 35,000 to 200,000 daltons. These proteins have no connection with those stated in this present invention.

The European patent application EP-A-0.112.784 concerns proteins extracted from the parasite after lysis of red cells. One of the categories is characterized by a mean molecular weight of the order of 50,000 plus or minus 5,000 daltons and is extracted from the parasite and not from the medium as in the invention. This category cannot be detected by the metabolic incorporation of $^{35}S$ methionine, whereas the protein according to the invention of a molecular weight of 50,000 daltons has exactly opposite properties, as will be seen in the following specification.

British patent application GB-A-2,099,300 relates to proteins of molecular weight between 180,000 and 250,000 daltons associated with the membranes of erythrocytic schizonts metabolised inside erythrocytes into smaller fragments associated with the merozoite membrane. These proteins are obtained by solubilization of infected erythrocytes and there is no relationship between these proteins and those stated in this invention.

The Rodriguez da Silva et al. paper (ref. 18) see page 32 mentioned previously relates to products derived from extracts of the parasite and the culture medium. The products identified in the supernatant were produced after, at the most, 6 hours following labelling, that is, well before the appearance of the antigens referred to in this invention. Specific monoclonal antibodies of these products recognize proteins of molecular weights different from those of the invention which are associated as regards certain of them with all the stages of the parasite, including its young stages, so that these products are totally different from those to which reference is made in the invention.

British patent application GB-A-2,114,288 describes a method for detecting circulating Plasmodium antigens by competitive inhibition, the antigens being extracted from the parasitized erythrocytes corresponding principally to the young forms. These antigens have cross-reactions with *Plasmodium* of rodents and other species of human *Plasmodium*, which in no way is the case in the present invention.

Patent application PCT WO-A-8,500,977 describes protein antigens of 41,000 and 58,000 daltons with Pi values of 4.7 to 5.5, which do not correspond those stated in this invention.

The invention therefore concerns antigens that can be isolated from the intraerythrocytic phase of *Plasmodium falciparum*, characterized in that they consist of:

a) a protein of having a molecular weight of 126 kDa to 130 kDa synthesized during the nuclear multiplication phase during schizogony and localized on the periphery of the schizonts at the parasitophorous vacuole level;

b) a protein having a molecular weight of 50 kDa having an isoelectric point of 5.5 appearing in the serum of patients infected by *Plasmodium falciparum* or in the culture medium of this microorganism during its intraerythrocytic phase c) a protein of 65 kDa separated by electrophoresis in reducing into two polypeptides (d) below at polypeptides of 47 and 18 kDa, appearing in the serum of patients infected by *plasmodium falciparum* or in the culture medium of this microorganism during its intraerythrocytic phase and d) the two polypeptides obtained by electrophoresis from said 65-68 kDa protein, one of said polypeptides having a molecular weight varying from 47 kDa to 50 kDa and the other polypeptide having a molecular weight of 18 kDa.

It has been found that a protein having a molecular weight varying from 126 kDa to 130 kDa is synthesized during the nuclear multiplication phase during schizogony and localized on the periphery of the schizonts at the parasithorous vacuole level. Proteolysis of the 126-130 kDa protein takes place at the moment of the merozoite release between 6 to 10 hours after having been synthesized and gives rise to two polypeptides of 50 kDa and 65-68 kDa of the invention. The 65-68 kDa fragment is comprises of the two polypeptides identified in d) above which polypeptides are covalently bound together by disulfide bonds. These proteolytic fragments are released in the culture medium and are never found in the parasitized cells.

It has also been found that the 50 kDa polypeptide in the 47-50 kDa fragment obtained from the 65-68 kDa protein is not identical to the protein of 50 kDa having an isoelectric point of 5.5.

It has been found that the protein of 126 kDa is proteolysed at the exact time of morozoite release, between 6 and 10 hours after having been synthesized, and is divided into two polypeptides, one of 50 kDa as described in b, above, and one of 65 kDa as described c in above which is itself made of two polypeptide chains of 47 and 18 kDa that are covalently bound by disulfide bridges. These proteolytic fragments are released in the culture medium and are never found in the parasitized cells.

The molecular weights of 126 kDa and 47 kDa defined above were determined on a special strain of *Plasmodium falciparum*, and namely, strain FCR-3 (J. B. Jensen et W. Trager, American Journal of Tropical Medicine and Hygien (1978), 27 (4), 743-6) and it was found that when other strains were used, these molecular weights could vary slightly, generally between 126 and 130 kDa, respectively 47 and 50 kDa. Thus, for example, values of 130 kDa and 50 kDa were found, for the commonly available strain *Plasmodium falciparum*ITUX-1 in which case a 50 kDa and a 68 kDa proteolytic fragments were found in the culture medium Consequently, in the continuation of the specification as well as in the claims, the definition "126 kDa protein" means any corresponding protein whose molecular weight, according to the strains, lies in particular between 126 kDa and 130 kDa and c) "65 kDa protein" likewise means any corresponding protein according to the strains and a molecular weight in particular between 65 kDa and 68 kDa.

By means of conventional techniques, it is possible to prepare from the supernatant of a parasite culture of *Plasmodium falciparum* an antigen obtained by affinity chromatography in a column containing IgGs of hyperimmun serum and use this antigen to obtain murine hybridomes producing specific antibodies either of the 50 kDa product or the 65 kDa product described herein above.

An example of obtaining and selecting such hybridomes is given as an indication in the experimental part (II) of this memorandum.

The 50 kDa, and 65 kDa products can be purified by passing the supernatant of the asynchronous culture of *Plasmodium falciparum* through an affinity chromatography column, in particular Sepharose 4B (Pharmacia), combined with specific antibodies respectively of the 50 kDa or 65 kDa product obtained by conventional means from hybridomes producing the corresponding monoclonal antibodies. As an indication, the antibodies can be present in the column at a rate of about 10 mg of IgG per ml of gel.

Likewise, the 126 kDa product can be purified by solubilisation of red cells parasitized by *Plasmodium falcioarum*, for example, by means of 0.5% sodium deoxycholate by passing the solution obtained through a column provided with monoclonal antibodies recognizing specifically the 50 kDa product and/or the 65 kDa product.

Specific polyclonal antibodies may also be used for these purifications. Examples of such purifications are given in the experimental part (III).

According to another of its features, the invention provides a method for the assay of antibodies against the proteins according to the invention, in particular the 50 kDa and 65 kDa products in the serum of subjects who have been or are being immunized.

Various well-known assay techniques involving immunological reactions may be used, such as for example the Radioactive Immuno Assay technique (RIA) using a radioactive label.

However, for the sake of simplicity and safety of the personnel, preference is given to a technique using one or several enzymes as a label. For example, in this concept, the various ELISA methods (Enzyme Linked Immuno Sorbent Assay) may be known.

One technique of this type which gives good results according to the invention comprises essentially the following stages consisting in:

1) fixing on a support a specific monoclonal antibody of the product 18, 47, 65, 50 kDa and/or 126 kDa) corresponding to the antibody to be assayed;

2) saturating the remaining free sites on the support;

3) reacting with an excess of antigen obtained from the supernatant of an asynchronous culture of *plasmodium falciparum*;

4) reacting the antigen fixed on the support at stage 3) with the medium to be tested;

5) reacting the whole with an enzyme-labelled human anti-immunoglobulin's antibody;

6) determining the quantity of specific antibodies present in the medium studied from the quantity of enzyme fixed on the support at stage 5, by means of a specific reaction of an enzyme, thanks to prior standardization.

The invention also provides a method for assaying 47, 50 and 65 kDa, 65 kDa products in the serum of patients, particularly during an onset of malaria, or in the culture medium, as well as a method for assaying the 126 kDa product in the erythrocytes, after solubilisation.

In all cases, use is made of immunological assays, in particular of the ELISA type.

According to a preferred mode of embodiment, such an assay essentially comprises the following stages consisting in:

1) fixing on a support a specific monoclonal antibody of the product to be assayed;

2) saturating the remaining free sites on the support;

3) reacting with the medium likely to contain the antigen to be assayed;

4) reacting the whole with the reference serum derived from an immune subject;

5) reacting with an enzyme-labelled human anti-IgG antiglobulin;

6) determining the quantity of antigen present in the medium studied from the activity of the enzyme by means of prior standardization.

In the experimental part (IV to VI) assays of this type concerning the 50 kDa and 65 kDa products are described purely for purposes of illustration.

The evolution of malaria in a patient can be studied by assaying at regular intervals the antigens according to the invention in his serum, for example, as indicated in the experimental part (VII). The work of the applicant led to the definition of the 50 kDa protein unit as being the quantity of 50 kDa product released over 24 hours by a culture of strain FCR-3 of *Plasmodium falciparum*, in a volume of 1 ml, with 6% hematocrit and an initial parasitemia of 7%.

According to another of its features, the invention provides a vaccine against malaria, characterized in that it comprises as active principle at least one of the 47, 65, 50 and 126 kDa proteins, preferably in the presence of an adjuvant.

Preferentially, each of the antigens is used alone or alternatively the 50 kDa and 65 kDa antigens together, for example, in equal quantities.

The adjuvant is preferably aluminium hydroxide (Al(OH)$_3$).

According to a preferred mode of embodiment of the invention, a 0.5 ml dose of vaccine contains:

0.5 to 1.5 mg, preferably 1 mg of 50 kDa and/or 65 kDa, or 126 kDa protein;

0.3 to 2 mg, preferably 1 mg, of aluminium hydroxide and a sufficient quantity of buffered isotonic aqueous solution.

As an example, an advantageous vaccination protocol consists in injecting a dose of vaccine three times successively at intervals of one month, with a booster one year after the third injection.

Advantageously, the injection is made by the subcutaneous route in the infra-spinous fossa or else in the external face of the forearm or thigh.

Intramuscular injection can also be considered.

Further details concerning the invention and examples of its application given purely as examples, are given in the experimental part that follows.

I—ANALYSIS OF ANTIGENS RELEASED IN THE CULTURE MEDIUM OF *PLASMODIUM FALCIPARUM* DURING AN ERYTHROCYTIC CYCLE

1. Culture of Parasite and Synchronization

The *plasmodium falciparum* strain FCR-3 (ref. 1) is cultured in human 0+ red cells with 6% hematocrit, 10% parasitemia, in RPMI 1640 medium (G. E. Moore et coll. JAMA, 199, 519 (1967)) with addition of 10% human A+ serum (W. Trager et J. B. Jensen, Science 193, 673-5 (1976)). The culture is synchronized by two treatments with sorbitol 27 hours apart (A. Vernes et coll., Am. J. Trop. Med. Hyg. 33, 197-203 (1984)).

2. Reinvasion Inhibition

The A. Vernes et al. (ref.4) is used. Synchronized cultures containing schizonts (100 µl per test, 1.5% hematocrit, 1% parasitemia) are exposed to normal or immune purified IgGs at different concentrations for 18 h, they are then washed and cultured in the normal medium for a further 8 h, then for 16 h in a medium with addition of radioactive precursor ($^{14}C$ isoleucine or $^3H$ hypoxanthine). The parasitized red cells are then collected with distilled water and the insoluble matter collected from the glass fibres (Mash company cell recuperator). The radioactivity in the organic liquid (mixture of solvents, of the Aqualuma type made by the Lumac company, was then measured by means of a Beckman LS-1800 type scintillation counter.

3. Labelling with $^{35}S$ Methionine

The erythrocytes obtained under 1 are resuspended in the culture medium with 1% hematocrit and distributed, in volumes of 5 ml into 25 cm$^3$ culture flasks. 30 hours after the second treatment with sorbitol, the erythrocytes are washed in medium not containing any methionine (RPMI 1640, "Selectamine kit" of the GIBCO company) and incubated for 5 hours in the same medium with addition of 40 µCi ml$^{-1}$ of $^{35}S$ methionine (>800 Ci mmol$^{-1}$, Amersham). A flask containing non parasitized red cells is treated in the same way as the control. At the end of the labelling period (t=O), one of the flasks is centrifuged (400 g, 10 minutes), the supernatant is collected and the labelled parasitized cells are resuspended in 5 ml of non-radioactive medium called "cold medium" and reincubated at 37° C. The supernatant is then replaced under the same conditions every 12 hours for 48 hours. A second flask is treated in the same way but, at each stage, a part of the parasitized red cells is also collected. Five pairs of samples are thus obtained at the end of 0, 12, 24, 36 and 48 hours respectively after the labelling period.

All these culture supernatants are centrifuged at 20000 g for 1 hour immediately after collection. The cells are washed and resuspended in serum-free RPMI medium. The supernatants and cell suspensions are adjusted to 0.6% of sodium dodecylsulfate (SDS) and heated at 100° C. for 10 minutes. After cooling they are adjusted to 0.5% SDS and 2.5% Triton X-100 (commercial name for a surfactant made by Rohm and Haas), according to the Erickson and Blobel method (A. H. Erickson et G. Blobel, J. Biol. Chem. 254, 11771-4 (1979)).

4. Purification of IgG and Preparation of Immunosorbant

The immunoglobulins were purified from plasma of a European donor living in an endemic malaria area (Madagascar) and from plasma of a non-immune control by ion exchange chromatography on DEAE trisacryl (Industrie Biologique Francaise) according to the Saint-Blancard et al. method (J. Saint Blancard et coll., Affinity Chromatography and Related Techniques, Elsevier, Amsterdam (1982) p. 305-312). The concentration of the IgG was measured by laser nephelometry (C. D. Deaton et coll. Clin. Chem. 22, 1465-71 (1976)).

The immunosorbants are prepared by combining these IgGs on Sepharose 4B (Pharmacia), activated with cyanogen bromide at the rate of 6 mg of proteins per ml of gel, according to the recommendations of the manufacturer.

5. Immunosorption

Each solubilised sample, corresponding either to 10 µl of parasitized cells or 5 ml of medium, is applied (using a recycling system) with two successive columns containing 10 µl of IgGs linked to Sepharose 4B, the first being prepared with non-immune IgGs (for non-specific adsorption), the latter with inhibiting IgGs (for immunosorption). Each gel is then washed five times with buffer containing 0.5% SDS and 2.5% Triton X-100 and eluted at 100° C. for three minutes in sample buffer for electrophoresis on polyacrylamide-SDS gel (SDS-PAGE) (U.K. Laemmli, Nature 227, 680-5 (1970).

6. SDS-PAGE and Fluorography

One-dimension SDS-PAGE analysis is performed in 12% acrylamide gels according to the Laemmli method (ref.8). Fluorography is then performed according to the R. A. Laskey et al. method (R. A. Laskey et coll., Eur. J. Biochem. 56, 335-341 (1975)).

The results obtained showed that 4 major antigens (140, 126, 108 and 70 kDa (kiloDaltons)) are recognized in the red cells by the immune IgGs at the end of labelling. Two of these (126 and 108 kDa) disappear during the first 12 hours of treatment in "cold medium", treatment called "chase". In the culture media, a major product of 50 kDa (accompanied by a less intense component of 47 kDa) appears after 12 hours and then diminishes. These two antigens are not observed in parasitized red cells.

7. Two-dimensional Electrophoresis

The eluate of the immunosorbant containing the supernatant obtained after 12 hours of "chase" is supplemented by 0.3% SDS, 9.95 M urea, 4% Nonidet P-40 (Shell company detergent), 2% Ampholines (LKB company, pH 3.5-10) and 0.1 M dithiothreitol (J. A. Garrels, J. Biol. Chem. 254, 7961-7977 (1979). Analysis by the two-dimensional PAGE technique is then performed according to the O'Farrel method (P. H. O'Farrel, J. Biol. Chem. 250, 4007-4021 (1975).

This analysis by the two-dimensional electrophoresis shows that the 50 kDa band is formed by a single protein of isoelectric 5.5 whereas the 47 kDa band is separated into two spots of about 5.9 and 6.1.

The radioactivity measured after precipitation with trichloroacetic acid (TCA) obtained from the supernatant and parasitized red cells obtained for 48 hours after labelling for 5 hours with $^{35}S$ methionine and from the corresponding immunoadsorbed eluates, is shown in the following Table I.

The distribution of the parasite stages is also reported for each sampling stage.

TABLE I

| Radioactivity[a] (c.p.m.) | 0 | "Chase" time (hours) | | | |
|---|---|---|---|---|---|
| | | 12 | 24 | 36 | 48 |
| Total ($\times 10^{-6}$) | | | | | |
| Culture medium | 2.22 | 11.2 | 7.2 | 2 | 1.1 |
| Erythrocytes | 63.6 | 20.8 | 9.2 | 8.2 | 2.2 |
| Immunoadsorbed eluates[b] ($\times 10^{-3}$) | | | | | |
| Culture medium | 147 (1) | 882 (1.5) | 167 (1.6) | 38.5 (0.8) | 18.9 (0.6) |
| Erythrocytes | 3944 (62) | 564 (62) | 302 (20.4) | 282 (14) | 43 (25) |
| Parasite stages[c] | | | | | |
| Rings | 3.5 | 89 | 55 | 26 | 46 |
| Trophozoites | 81 | 4 | 43 | 72 | 43 |
| Schizonts | 15.5 | 7 | 2 | 2 | 11 |

[a]Each value reported represents the total content of the culture flask
[b]Non-specific adsorption values given in brackets
[c]Percentage of total parasitemia.

II—PRODUCTION OF SPECIFIC MURINE HYBRIDOMES OF TWO 50 kDa AND 65 kDa PRODUCTS EXCRETED BY PLASMODIUM FALCIPARUM IN IN-VITRO CULTURE AND THEIR COMMON PRECURSOR IN THE PARASITE.

1. Material and Methods a.) Mice

BALB/C(IFFA-CREDO) mice were used both for obtaining immune lymphocytes and the in vivo production of monoclonal antibodies. They were 6 to 12 weeks old.

b.) Antigen

The antigen used to immunise the mice was obtained by a culture of the Plasmodium falciparum strain FCR-3 on group Rh positive human red cells in an RPMI 1640 medium with addition of group A human serum according to the Trager and Jensen technique (ref. 3). The parasite culture was synchronized by two treatments with sorbitol according to Vernes et al. (ref. 4). The antigen was purified from 50 ml of supernatant collected just after reinvasion while the culture hematocrit was 2% and 10% of the red cells contained schizonts. Purification by affinity was carried out by passing this supernatant through a column prepared with the IgGs of hyper immune human serum serving as reference.

The material obtained, after having been divided into three equal aliquot fractions was used to immunise a mouse according to the following protocol: two intraperitoneal injections were made with Freund complete adjuvant at days 0 and 21, followed by an intravenous injection 7 days later.

c.) Cell Fusion and Culture of Hybrids

Three days after the third injection, the mouse was sacrificed and the spleen taken under sterile conditions. After grinding the spleen and washing the cells thereby obtained in serum free medium, the splenocytes were counted and mixed with non-secreting murine myeloma NS-1 cells (G. Kohler et coll. European J. of Immunology, 6, 292, (1976) in a ratio of 10 splenocytes to one NS-1 cell. Fusion was permitted by the use of polyethyleneglycol 1500 (Merck) and dimethylsulfoxide and obtained according to the technique described by Galfre et al. (Galfre et coll. Nature 226 550 (1977) After fusion, the cells washed in the presence of calf foetal serum (CFS) were distributed uniformly into the wells of 4 flat-bottomed microtitration plates (Costar, ref. 12 905-96, Flobio, France) containing since 24 hours a feeding layer of peritoneal macrophages from non-immune BALB/C mice (5000 cells per well) (Fazekas de St. Groth et coll., J. of Immunological Methods, 35, 1 (1980)).

The culture proceeded for 24 hours in a Dulbecco modified Eagle medium (R. Dulbecco et coll., Virology 8, 396 (1959) containing 10% CFS. This medium was supplemented with non-essential amino acids, sodium pyruvate, 1-glutamine, penicillin, streptomycine as well as hypoxanthine and thymidine (medium called hereinafter HT).

From the following day the non-fused myelomatous cells were removed by adding aminopterine in HT medium to obtain a HAT medium according to Littlefield J. Littlefield, Science 145, 709 (1964).

The cells of the positive fusion wells in breeding tests were cloned twice by limited dilution. After the first cloning, the cells selected were progressively cleaved into aminopterine and cultivated in HT medium.

The cells were deep-frozen according to the following protocol: cooling at $+4°$ C., centrifuging at 400 g for 10 minutes, taking up the centrifuging residue in a 10% DMSO mixture and 90% CFS previously maintained at $0°$ C., followed by distribution in aliquot fractions. The tubes (Nunc, Bio-block, France) were allowed to remain at $-80°$ C. for 24 hours and then stored in liquid nitrogen.

d.) Screening of Hybrids

Several tests were used systematically throughout this work for screening hybrids.

Immunofluorescence (IF) and immunoelectrotransfer ("blot") with supernatants of cultures of P. falciparum, strain FCR-3. The hybridomes were systematically characterized by immunoprecipitation on the one hand of extracts solubilized by a detergent (Nonidet P-40) of parasite types labelled for 5 hours with $^{35}S$ methionine and on the other hand of the supernatant of liquid labelled for 4 hours with $^{35}S$ methionine and "chased" for 12 hours.

A serum of a rabbit murine anti-IgGs combined with protein A-sepharose 4B (Pharmacia) was used. Electrophoresis in polyacrylamide gel (SDS-PAGE) was performed by fluorography (immuno-precipitation).

e.) Production of Purified Monoclonal IgGs

For the mass production of monoclonal antibodies, the mice were first innoculated by the intraperitoneal route with 0.5 ml of pristane (2, 6, 10, 14-tetramethylpentadecane) (Serva, Tebu, France). 15 days later, the cells ($5.10^6$) were injected by the same route.

The ascites were collected from the 15th day onwards, regrouped and centrifuged at 1500 g for 30 minutes at $+4°$ C.

The IgGs were purified by ion exchange chromatography in a DEAE-TRISACRYL column (IBF France). After checking for purity by electrophoresis in polyacrylamide gel, the protein concentrations were measured by means of the "Bio-Rad Protein Assay") of the Bio-Rad Company. The samples of these IgGs were preserved at $-80°$ C. before use.

2. Results

Of the 39 hybridomes having shown specific immunological activity of *Plasmodium falciparum*, 2 were more specially selected because of their specificity for the 50 kDa and 65 kDa products excreted by *Plasmodium falciparum* in culture and their common precursor in the parasite.

The characteristics of these two hybridomes are summarized in the following table II:

TABLE II

CHARACTERIZATION OF THE SPECIFIC HYBRIDOMES OF THE 50 kDa AND 65 kDa PRODUCTS EXCRETED IN THE CULTURE MEDIUM BY *Plasmodium falciparum* AND THEIR INTRACELLULAR PRECURSOR

| Hybridome | 23D5 2H6 | 3E9 1A11 |
|---|---|---|
| Sub-class | IgG# | IgG$_1$ |
| Product recognized in the parasites ("Blot" and immuno-precipitation) | 126 kDa | 126 kDa |
| Product recognized in the culture medium ("Blot" and immuno-precipitation) | 50 kDa (126 kDa traces##) | 65 kDa (126 kDa traces##) |
| Immunofluorescence on parasitized red cells | Periphery of aged schizonts and intracellular merozoites. | |

\# probably IgG$_2$

\#\# Under the culture conditions, the 126-50 kDa conversion was not complete, which may reflect the partial inadequacy of the in vitro culture conditions for the optimal multiplication of the parasites.

III—PURIFICATION OF THE 50 kDa, 65 kDa AND 126 kDa ANTIGENS

1. Purification of 50 kDa Antigen

The culture medium is passed first of all through a Sepharose 4B column (Pharmacia) not including any protein, then through a Sepharose 4B column and combined with monoclonal antibodies produced by, the hydridome 23D5 2H6 of Table II, at a rate 10 mg of IgG per ml of gel.

Washing is then effected and followed by elution with 0.1 M diethylamine, pH 11.2, dialysis and concentration.

2. Purification of 65 kDa Antigen

The same procedure is followed using a column provided with monoclonal antibodies produced by the hybridome 3E9 1A11 of Table II.

3. Purification of 126 kDa Antigen

The procedure followed was as before replacing the culture medium by parasitized red cells solubilized in 0.5% sodium deoxycholate and using either of the monoclonal antibodies indicated above.

IV—ASSAY OF SPECIFIC ANTIBODIES OF THE 50 kDa PRODUCT EXCRETED BY *PLASMODIUM FALCIPARUM* IN THE IN-VITRO CULTURE MEDIUM BY AN IMMUNO-ENZYMATIC TECHNIQUE (ELISA)

1. Material a) Monoclonal Antibody

Clone 23D5 2H6 was selected for the assay of anti 50 kDa human antibodies of *Flasmodium falciparum*.

b) The Antigen

The antigen used to assay the specific human IgGs by immunocapture was a supernatant of the asynchronous culture of *Plasmodium falciparum*. The culture conditions were as follows:

Time 0:
hematocrit 6% (human O Rh+ red cells)
parasitemia 7% (strain FCR-3)
fresh medium
Collection at 24th hour.

The culture is then centrifuged (600 g for 30 minutes at +4° C.). The supernatant collected in this way was divided into aliquot fractions and deep-frozen at 8° C. before use.

c) The Reference Serum

In order to diminish assay variations during various manipulations, the result of each serum was compared with that of a reference serum tested systematically in parallel on each plate.

This reference serum was the previously described hyper-immune serum, it being considered here as "100% antibody".

A serum from a child aged 7 years having always lived in metropolitan France and without any known pathological antecedent was also tested on each plate. It was used to measure the background noise.

d) Sera tested 178 sera were tested during this study. They were derived from patients of known age and are listed in Table II.

50 came from France and had been taken either from new-borns (5) or young adults (45), without any known history of malaria (control group).

108 sera were taken in Gabon in the Franceville region. The age distribution is given in Table III.

20 sera of various geographical origins came from patients suffering a first attack of malaria.

These sera were divided into samples as soon as they had been taken and maintained at −20° until they were used.

As regards 38 sera, taken from these three categories, it was possible to perform immuno-precipitation both from the culture medium and the red cells parasitized by *Plasmodium falciparum*, strain FCR-3. The immuno-precipitation technique is described above.

e) The ELISA Technique Used

The anti 50 kDa antibodies of *Plasmodium falciparum* were quantified in flat-bottomed micro-titration plates (Costar, Flobio, France).

These plates were sensitized in a volume of 200 µl without prior treatment, by a 6.25 gamma/ml solution of purified IgGs obtained from the hybridome 23D5 2H6 in a 0.15 M PBS buffer (saline phosphate buffer), pH 9.6. After incubation at +4.C, for more than 18 hours, the wells were washed with demineralized water containing 0.05% Tween 20 (commercial name for sorbimacrogol laurate, Serva, Tebu, France) then dried rapidly by turn-over (washing). They were then saturated for 2 hours at 37.C with a 5% solution of bovine albumin in a PBS buffer, pH 7.2, 0.15 M (PBS) (200 ul per well).

After a further period of washing, the antigen was immunocaptured by diluting it to 1/10 in PBS containing 0.1% Tween 20 and 1% bovine albumin (PBS-T-A). 200 µl of this dilution were then distributed into each well, the plates then being allowed to remain at +4° C. for 18 hours.

After a further wash, the sera, diluted to 1/200 in PBS-T-A (PBS-Tween-Albumin), were deposited in a volume of 200 µl per well in duplicate and allowed to incubate for two hours at 37° C.

An identical washing operation preceded the deposit of the antiglobulin conjugated with peroxidase (goat antibody and human anti chaine gamma), (Tago, Biosoft, Paris): 200 ul per well, dilution to 1/3000 in PBS-T-A. After incubation for 90 minutes at 37° C., the plates were washed and the presence of peroxidase detected by oxidation of ortho-phenylene diamine (OPD) by pouring into each 200 µl well the following solution:

| citrate-phosphate buffer pH 5 | 10 ml |
|---|---|
| Ortho-phenylene diamine | 4 mg |
| hydrogen peroxide 110 V (freshly prepared). | 15 µl. |

After incubation for 10 minutes in darkness at ambient temperature, the enzyme reaction was stopped by the addition of 50 µl of 2N sulfuric acid to each well.

The optical density of each well was measured directly through the plate via a photometer (DYNA-LAB) at a wavelength of 492 nm.

f) Expression of Results

For each serum studied, the optical density (OD) taken was the mean of those two corresponding wells, less the background noise measured under the same conditions on a negative serum. This OD was compared with that of the reference serum present on the same plate.

The percentage obtained was used as a mode of expression of the results of the assay of the specific human antibodies of the 50 kDa product excreted by *Plasmodium falciparum* in the culture.

2. Results

TABLE III

| Group | Number | ELISA Mean % ref. | ELISA S.D. % ref. | Immuno precipitation 50 & 126 kDa |
|---|---|---|---|---|
| Controls | 50 | 0.21 | 0.91 | 0/5 |
| Onset of malaria (first invasion) | 20 | 0.40 | 1.18 | not done |
| G 3 to 30 mths | 26 | 2.15 | 3.5 | 5/12 |
| A 3 to 9 yrs | 9 | 17.16 | 11.4 | 7/8 |
| B more than 10 yrs | 35 | 36.94 | 33.95 | 7/7 |
| O Mothers (at childbirth) | 19 | 19.42 | 5.46 | 3/3 |
| N Cords (New-borns) | 19 | 22.9 | 15.83 | 3/3 |

The results summarized in Table III show the importance of the assay of the anti 50 kDa antibodies of *Plasmodium falciparum* for determining immunity against this parasite.

The group of control subjects are seen to be negative. The same applies to the group of 20 subjects suffering from an attack of malaria, although it was the only patient with a first infection dating from several days previously for which the specific antibodies have been found.

Furthermore, this study showed the presence of anti 50 kDa antibodies in the umbilical cord of new-borns, at a rate comparable to that of the mothers at childbirth.

The evolution of the specific antibodies of the 50 kDa product, measured by ELISA, according to age, is comparable to the evolution of palustal immunity in the same region of Gabon: appearance of immunity from 3 years. This correlation was found in a recent study on 73 children from holo-endemic areas of Nigeria.

V—ASSAY OF 50 kDa PRODUCT EXCRETED BY *PLASMODIUM FALCIPARUM* IN-VITRO IN THE CULTURE MEDIUM BY AN IMMUNO-ENZYMATIC TECHNIQUE (ELISA)

1. Material a) The Monoclonal Antibody

Clone 23D5 2H6 was selected for the assay of the 50 kDa antigen excreted by *Plasmodium falciparum*.

b) Reference Antigen

The antigen used as reference in the assay of the 50 kDa product by immunocapture, was a supernatant of the asynchronous culture of *Plasmodium falciparum*, strain FCR-3. The culture conditions were as follows:
Time 0:
hematocrit 6% (human red cells)
parasitemia 7% (strain FCR-3)
Fresh medium
Collection at 24th hour.

The culture was then centrifuged (600 g for 30 minutes at +4° C.). The supernatant collected in this way was divided into aliquot fractions and deep-frozen at −80° C. until it was used.

By arbitrary definition, a concentration of 1 50 kDa unit per ml (1 U50) is allocated to this medium.

c) Human Polyclonal Serum

The immunoabsorbed antigen was detected by the monoclonal antibody by means of a human hyper immune serum used as reference in this study and described above.

d) Immuno Enzymatic Technique

The 50 kDa antigen of *Plasmodium falciparum* was quantified in flat-bottomed microtitration plates (MICRO ELISA NUNC Poly Labo Block).

These plates were sensitized in the volume of 200 µl without any prior pretreatment by a solution of purified IgGs of hybridome 23D5 2H6 (10 gamma/ml) in 0.15 M, PBS buffer, pH 9.6). After incubation at +4.C for more than 18 hours, the wells were washed in PBS buffer, pH 7.2, 0.15 M (PBS), then saturated for 2 hours at 37° C. with a 5% solution of bovine albumin in PBS (200 µl per well).

The plates were then washed with a 0.05% solution of Tween 20 (Serva) in demineralized water, then dried rapidly by turning over (washing).

A range of dilutions in PBS containing 0.1% Tween 20 (Serva) and 2% bovine albumin (PBS-T-A) was prepared both from the reference antigen (dilutions 1/10 to 1/1280) and from the various media tested. Each dilution was tested in two different wells (duplicate) in a volume of 200 µl. The plates filled thereby were then incubated for one night at +4° C.

After this incubation, the plates were washed. 200 µl of a dilution in PBS-T-A of the reference serum were then poured into each well tested. The plates were then allowed to remain at 37° C. for 2 hours.

An identical washing operation preceded the deposition of the antiglobulin conjugated with the peroxidase (goat antibody human gamma anti chain), (Tago, Biosoft, Paris): 200 μl per well, dilution 1/3000 in PBS-T-A.

After incubation for 90 minutes at 37° C., the plates were washed. The presence of peroxidase was detected by oxidation of ortho-phenylene diamine (OPD) by pouring into each well 200 μl of the following freshly prepared solution:

| citrate-phosphate buffer pH 5 | 10 ml |
| ortho-phenylene diamine | 4 mg |
| hydrogen peroxide 110 V | 15 μl |

After incubation for 10 minutes in darkness at ambient temperature, the enzyme reaction was stopped by the addition of 50 μl of 2N sulfuric acid to each well.

The optical density of each well was measured directly through the plate by a photometer (DYNALAB) at a wavelength of 492 nm.

e) Quantification of the concentration of the 50 kDa product of *Plasmodium falciparum*.

For each dilution tested, the mean optical densities (OD) of the corresponding duplicate was calculated with subtraction of the optical density of the negative control medium.

From the various dilutions of the reference medium, a standardization curve establishing a relationship between the OD and the logarithm of the 50 kDa product concentration of this medium was plotted (Apple IIe computer programe). Consideration was given only to the 50 kDa product concentration corresponding to the linear part of the curve.

An analogous curve was plotted for the media studied. Only the points corresponding to the linear portion of the OD/logarithm of dilution of medium curve were considered int the calculation of the concentration of the 50 kDa product of *Plasmodium falciparum*, by comparison with the previously described standardization curve.

The concentration measured was the mean concentrations measured from these various points.

2) Results

In this example, the standard range was established from dilutions of the reference medium between 1/lo and 1/640. The statistical analysis has shown that there is no linear relation (P<0.1) between the OD (at 492 nm) and the logarithm of the dilution in this range, the relation which is confirmed when the optical density variations are plotted against the logarithm of the dilution.

A culture of *Plasmodium falciparum* was followed for 4 days. The medium was changed completely at precise times while the parasitemia was measured. The supernatants were deep-frozen at −80° C. and analyzed simultaneously from 4 dilutions (1/10 to 1/80). Table IV gives the concentration of the 50 kDa product released by the FCR-3 strain of *Plasmodium falciparum* in supernatant of the in-vitro culture against the culture time and the initial parasitemia (hematocrit constant at 6%).

The study of the results obtained in this way has made it possible to show the very good reproducibility of the method, its sensitivity and the relationship between the culture time, parasitemia and the quantity of 50 kDa product released in the culture medium.

The 50 kDa (U50) unit has thus been defined as the quantity of 50 kDa released over 24 hours by a culture of the FCR-3 strain of *Plasmodium falcicarum* in a volume of 1 ml, with 6% hematocrit and 7% parasitemia.

It is understood that the 50 kDa product is considered here as such or as being part of its precursor of 126 kDa in sofar as this latter is present as traces in the culture supernatants and in which the monoclonal antibody recognizes the two products equally well.

TABLE IV

The study of the release of the 50 kDa product in the supernatant of a culture medium against time and parasitemia

| Exp. | Culture duration (h) | Initial parasitemia % | Concentration U 50 kDa/ml |
|---|---|---|---|
| 1 | 24 | 0 | 0 |
| 2 | 16.5 | 0.11 | 0.03 |
| 3 | 7.5 | 0.21 | 0.03 |
| 4 | 7.5 | 0.44 | 0.07 |
| 5 | 6.5 | 0.75 | 0.05 |
| 6 | 16.5 | 1.68 | 0.25 |
| 7 | 7.2 | 2.75 | 0.13 |
| 8 | 17.7 | 5.05 | 0.55 |

This table shows that the concentration of the 50 kDa product increases on the one hand with the culture duration and, on the other, with the initial parasitemia.

VI—ASSAY OF 65 kDa PRODUCT EXCRETED BY *PLASMODIUM FALCIPARIUM* IN VITRO IN THE CULTURE MEDIUM

This assay is performed according to the protocol described under V but using a specific monoclonal antibody of the 65 kDa product, for example, clone 3E9/1 All described in Table I.

VII—STUDY OF THE EVOLUTION OF MALARIA IN A PATIENT BY ASSAY OF THE CONCENTRATION OF 50 kDa (or 65 kDa) PRODUCT IN THE SERUM.

The study carried out concerned three patients in the course of treatment by classic anti-malarials (quinine, sulfate and chloroquine). The serum was assayed under the same conditions as those described earlier (V or VI) in the case of the culture medium, but at serum dilutions of 1/40 and 1/10.

During the acute phase of the disease it was observed that the serum of patients contained 0.1 to 0.3 units of 50 kDa (U50) (as defined earlier in para V) per ml.

By performing regular repeated assays, it was found that the 50 kDa products disappeared progressively from the serum of patients and that the disappearance was total after 4 to 6 days of treatment.

VIII—STUDY OF 126 kDa PRODUCT AND ITS RELATIONSHIP WITH THE 50 kDa PRODUCT

1. Modes of 126–50 kDa Conversion

An asynchronous culture was labelled for 6 hours with $^{35}S$ methionine. The schizonts were there isolated by centrifuging on a metrizamide mat. These schizonts were then reincubated for 16 hours under normal culture conditions, either alone (in that case, only the release of merozoites was involved) or in the presence of healthy red cells (in that case, reinvasion occurs). On completion of incubation, the culture medium was immunoprecipitated by the IgGs of an immune individual or by the monoclonal antibodies derived from a clone selected as indicated earlier. No difference was observed between these two schizonts' incubation times: the 126–50 kDa conversion is therefore a consequence of the release of merozoites not of the reinvasion of erythrocytes.

During the same experiment, a part of the radio labelled schizonts was deep-frozen in the culture medium and then incubated for 16 hours at 37° C. The 50 kDa product does not appear under these conditions whereas the 126 kDa was released in the medium during freezing. It seems therefore that the 126-50 kDa version requires the spontaneous release of merozoites and is not a proteolysis of the 126 kDa in the culture medium.

2. Kinetics of the Biosynthesis of the 126 kDa Product

An asynchronous culture was labelled with $^{35}S$ methionine for 30 minutes, resuspended in the culture medium and distributed in 8 equal volumes which were incubated at 37° C. and sampled successively after 0, 5, 6, 7, 8, 9, 10 and 11 hours of "chase". After solubilisation, the cells and the media of each sample were immunoprecipitated by a monoclonal antibody obtained as indicated previously.

The 126 kDa protein appears in the red cells from the end of labelling and persists in it for 10 hours of "chase". The 50 kDa appears in the medium from 6 hours of "chase".

Since the 126-50 kDa conversion takes place during the merozoites release - reinvasion phase, kinetic studies showed that the 126 kDa protein is synthesized during about 4 hours, from 32 to 36 hours, the intraerythrocytic cycle lasting 42 hours. This phase corresponds to the nuclear multiplication phase during schizogony.

3. Localization of 126 kDa Product a) Selective Hemolysis with Saponine

A short incubation (5 minutes, 20° C.) in a 0.1% saponine solution lyses in the red cells but does not degrade the parasites and, in particular, does not release any major antigen of 195 kDa present on the surface of the schizonts R. J. Hoard et coll., Molec. Bioch. Parasit. 11, 349-362 (1984)).

Parasitized red cells radio labelled with $^{35}S$ methionine (asynchronous culture, labelling for 3 hours, "chase" 2 hours) are treated with 0.1% saponine in PBS at 20° C. for 5 minutes. Parasites and lysis of supernatant are then separated by centrifuging and analyzed by immuno precipitation by a monoclonal antibody obtained as indicated above.

The 126 kDa product is found in the saponine supernatant, which suggests a vacuolar localization (or in the parasitophore vacuole membrane).

b) Electron Microscopy

This technique makes it possible, using here again a monoclonal antibody, to localize the 126 kDa product on the periphery of the schizonts, at the parasitophore vacuole level (detection by "indirect immunoperoxidase" after fixation with paraformaldehyde-glutaraldehyde, and permeabilization with saponine).

IX—PRODUCTION OF SPECIFIC POLYCLONAL ANTIBODIES OF THE 126 kDa PROTEIN AND IDENTIFICATION IN THE CULTURE MEDIUM OF ITS PROTEOLYTIC FRAGMENTS.

About 1 mg of 126 kDa protein purified as specified in section III PURIFICATION OF 50, 65 AND 126 kDa ANTIGENS were injected into a rabbit according to the method supplied by Vaitukaitis (Rodriguez Da Silva et coll., Bull WHO, 61, 105-112 (1983)), the antibodies collected were used for immunoprecipitating the supernatant of a methionine and labelled culture as described in section VIII para 1. Moment of appearance of 50 kDa product. The results of the immunoprecipitation showed that the polyclonal serum prepared in the rabbit against the 126 kDa molecule recognizes under reducing conditions three polypeptides of molecular weights respectively of 50 kDa, 47 kDa and 18 kDa. This demonstrates that the conversion of the 126 kDa product gives rise to three fragments respectively of 50, 47 and 18 kDa. A further precision was provided by electrophoresis under non-reducing conditions, when the polyclonal antibody recognizes a product of 50 kDa and a product of about 65 kDa which is therefore constituted by the combination of the 47 and 18 kDa products by means of a disulfide bond.

BIBLIOGRAPHY (1) J. B. Jensen et W. Trager, American Journal of Tropical Medicine and Hygien (1978), 27 (4), 743-6
(2) G. E. Moore et coll. JAMA, 199, 519 (1967)
(3) W. Trager et J. B. Jensen, Science 193, 673-5(1976)
(4) A. Vernes et coll., Am. J. Trop. Med. Hyg. 33, 197-203 (1984).
(5) A. H. Erickson et G. Blobel, J. Biol. Chem. 254, 11771-4 (1979)
(6) J. Saint Blancard et coll., Affinity Chromatography and Related Techniques, Elsevier, Amsterdam (1982) p. 305-312
(7) C. D. Deaton et coll., Clin. Chem. 22, 1465-71(1976)
(8) U. K. Laemmli, Nature, 227, 680-5 (1970)
(9) R. A. Laskey et coll., Eur. J. Biochem. 56, 335-341 (1975)
(10) J. A. Garrels, J. Biol. Chem. 254, 7961-7977 (1979)
(11) P. H. O'Farrel, J. Biol. Chem. 250, 4007-4021 (1975)
(12) G. Kohler et coll., European J. of Immunology, 6, 292, (1976)
(13) Galfre et coll., Nature, 226, 550 (1977)
(14) Fazekas de St. Groth et coll., J of Immunological Methods, 35, 1 (1980)
(15) R. Dulbecco et coll., Virology 8, 396 (1959)
(16) J. Littlefield, Science 145, 709 (1964).
(17) R. J. Howard et coll., Molec. Bioch. Parasit. 11, 349-362 (1984).
(18) Rodriguez Da Silva et coll., Bull WHO, 61, 105-112 (1983).

What is claimed:

1. An antigenic protein isolated from the intraerythrocytic phase of *Plasmodium falciparum*, comprising a protein having a constant molecular mass of 50 kDa whatever the strains used and an isoelectric point of 5.5, said protein originating exclusively in the serum of a patient infected by *Plasmodium falciparum* or in the culture medium of this microorganism during its intraerythrocytic phase, at the time of the merozoite release, said protein being obtained by proteolysis of a precursor protein which has a molecular weight varying from 126 kDa to 130 kDa and which precursor is synthesized during the nuclear multiplication phase during schizogony and localized on the periphery of the schizonts at the parasitophore vacuole level, wherein said antigenic protein is specifically reactive with the monoclonal antibody produced by clone 23D52H6.

2. A vaccine against malaria, comprising an effective amount of an active ingredient comprising the antigenic protein of claim 1 and an effective amount of an immunologically acceptable carrier.

3. A vaccine against malaria in 0.5 ml dosage unit form comprising about 0.5 to 1.5 mg of the antigenic protein of claim 1;
about 0.3 to 2 mg aluminum hydroxide; and
the balance, a buffered isotonic aqueous solution.

* * * * *